(12) United States Patent
Hovanes et al.

(10) Patent No.: US 7,166,123 B2
(45) Date of Patent: Jan. 23, 2007

(54) SYSTEM AND METHOD FOR CONTROLLING PRESSURE IN A SURGICAL TOURNIQUET USING A REMOTE UNIT

(75) Inventors: Michael E. Hovanes, Redmond, WA (US); Don S. Schmitt, Wauwatosa, WI (US)

(73) Assignee: Instrumed, Redmond, WA (US)

( * ) Notice: Subject to any disclaimer, the term of this patent is extended or adjusted under 35 U.S.C. 154(b) by 510 days.

(21) Appl. No.: 10/290,117

(22) Filed: Nov. 7, 2002

(65) Prior Publication Data

US 2003/0236548 A1 Dec. 25, 2003

Related U.S. Application Data

(63) Continuation-in-part of application No. 09/504,131, filed on Feb. 15, 2000, now Pat. No. 6,475,228, which is a continuation of application No. 09/280,312, filed on Mar. 29, 1999, now Pat. No. 6,051,016.

(51) Int. Cl.
*A61B 17/00* (2006.01)

(52) U.S. Cl. .................................... 606/202
(58) Field of Classification Search ........ 606/201–203; 601/150, 148, 149
See application file for complete search history.

(56) References Cited

U.S. PATENT DOCUMENTS

| 4,321,929 | A | 3/1982 | Lemelson et al. |
|---|---|---|---|
| 4,469,099 | A | 9/1984 | McEwen |
| 4,479,494 | A | 10/1984 | McEwen |
| 4,605,010 | A | 8/1986 | McEwen |
| 4,671,290 | A | 6/1987 | Miller et al. |
| 4,770,175 | A | 9/1988 | McEwen |
| 4,869,265 | A | 9/1989 | McEwen |
| 5,048,536 | A | 9/1991 | McEwen |
| 5,181,522 | A | 1/1993 | McEwen |
| 5,307,791 | A | 5/1994 | Senoue et al. |
| 5,312,431 | A | 5/1994 | McEwen |
| 5,352,195 | A | 10/1994 | McEwen |
| 5,366,474 | A | 11/1994 | Blemenkranz et al. |
| 5,439,477 | A | 8/1995 | McEwen |
| 5,454,831 | A | 10/1995 | McEwen |
| 5,556,415 | A | 9/1996 | McEwen et al. |
| 5,578,055 | A | 11/1996 | McEwen |
| 5,584,853 | A | 12/1996 | McEwen |
| 5,607,447 | A | 3/1997 | McEwen et al. |
| 5,649,954 | A | 7/1997 | McEwen |
| 5,681,339 | A | 10/1997 | McEwen et al. |
| 5,741,295 | A | 4/1998 | McEwen |
| 5,855,589 | A | 1/1999 | McEwen |
| 5,911,735 | A | 6/1999 | McEwen et al. |
| 5,968,073 | A * | 10/1999 | Jacobs ................. 606/202 |
| 6,589,267 | B1 * | 7/2003 | Hui ..................... 606/202 |

* cited by examiner

*Primary Examiner*—Kevin Truong
(74) *Attorney, Agent, or Firm*—Reed Smith LLP

(57) ABSTRACT

The present invention is a surgical tourniquet controller which receives operational parameters from a remote unit, allowing flow components associated with controlling a surgical tourniquet to be collocated with a surgical tourniquet in use, while allowing an operator of the tourniquet to operate the flow components from a remote location, such as at an anesthesiologists position, thus reducing the involvement of the surgical tourniquet operator from the surgical field.

45 Claims, 8 Drawing Sheets

SYSTEM AND METHOD FOR CONTROLLING PRESSURE IN A SURGICAL TOURNIQUET USING A REMOTE UNIT

The present application is a continuation in part of U.S. patent application Ser. No. 09/504,131 filed Feb. 15, 2000 now U.S. Pat. No. 6,475,228, which is a continuation of U.S. patent application Ser. No. 09/280,312 filed Mar. 29, 1999. U.S. patent application Ser. No. 09/280,312 issued as U.S. Pat. No. 6,051,016 on Apr. 18, 2002.

FIELD OF THE INVENTION

The present invention is directed to surgical tourniquet controllers, and more particularly to surgical tourniquet controllers having spatially separated operator control interfaces and fluid pressure controllers to allow management of equipment and operators adjacent to the surgical field.

BACKGROUND

Surgical tourniquets are used to provide a bloodless field for surgical procedures involving the extremities of the human body. The tourniquets function by compressing an extremity sufficiently to collapse blood vessels in the area of the tourniquet, thus preventing the flow of blood past the tourniquet.

A tourniquet being used during surgery must be monitored by a trained operator, typically an anesthesiologist. The function of the anesthesiologist is not limited to monitoring the tourniquet, but may also involve the administration of anesthesia to a patient, as well as the monitoring of the patient vital signs during the procedure.

Typically, the position of an anesthesiologist during a surgical procedure is away from the surgical field. Although surgical tourniquets are typically used on extremities, the location of the anesthesiologist is adjacent to the head of the patient, as shown in FIG. 1. This location generally assists in the reduction of congestion in the surgical field.

Siting the location of the controller associated with the surgical tourniquet is determined by the necessity to minimize the amount of equipment located in the surgical field, while also minimizing the length of the tubing necessary to provide a supply of a pressure medium to the tourniquet cuff. Accordingly, the surgical tourniquet controller is generally located near the perimeter of the surgical field to limit the amount of tubing required between the controller and a surgical cuff or cuffs. Locating the controller adjacent to the surgical field, however, also may require that an operator approach the surgical field to operate the control interface of the controller.

Additionally, the proximity of the surgical tourniquet controller to the surgical field results in the size and configuration of the controller having an effect on procedures within the surgical field. Reducing the size of the controller may reduce the impact the physical proximity of the controller to the surgical field will have, however may also adversely affect the suitability of the operator controls, displays, or interface. Finally, the configuration of the controller itself may be an issue in ensuring cleanliness in the area proximate to the surgical field.

In addition to the surgical tourniquet controller being in the operating room when a surgical procedure using a surgical tourniquet is being performed, other electronic equipment will likely be present, such as EKG monitors, EEG monitors, breathing monitors, and automated intravenous injection equipment, including equipment being used to administer anesthesia. Much of this equipment needs to be monitored to ensure its proper functioning, typically by the anesthesiologist responsible for the administration of anesthesia. If this equipment is distributed throughout an operating environment, operator task loading may increase unless additional personnel are provided. Including additional personnel in the operating environment, however, may also increase congestion for other personnel in the environment.

Due to the sensitivity of the operating environment, the potential of stray radio frequency emissions adversely affecting other electronic equipment must be minimized. Excesses of cabling may also be also undesired, due to the added complexity of ensuring that the cabling is accurately routed and connected, due to cleanliness issues associated with the cabling, and due to potential impacts the cabling may have on the operating environment, such as the creation of trip hazards.

SUMMARY OF THE INVENTION

The present invention is a surgical tourniquet controller which receives operational parameters from a remote unit, allowing flow control components associated with controlling a surgical tourniquet to be located adjacent to with a surgical tourniquet in use, while allowing an operator of the tourniquet to operate the flow components from a remote location, such as at an anesthesiologist's position, thus reducing the involvement of the surgical tourniquet operator near the surgical field.

The present invention may be embodied in a surgical tourniquet controller having a flow control unit located adjacent to the surgical field, and a remote unit for providing an operator interface to the flow control unit. The flow control unit may include at least one pressure control valve for regulating the pressure in a surgical tourniquet attached to the flow controller via a channel allowing the transmission of a fluid (including gasses). The regulation of the pressure in the surgical tourniquet cuff may be accomplished by the valve opening to allow a higher pressure medium to be exposed to the fluid channel, thus allowing the higher pressure medium to enter the fluid channel, increasing the pressure in the fluid channel. As the fluid channel is connected to the pressure cuff, the pressure in the pressure cuff will increase. The lowering of the pressure in the pressure cuff may be accomplished in any of several fashions, including the provision of a constant bleed-down condition, the provision of an exhaust channel from a surgical tourniquet cuff to the environment controlled by an exhaust valve, or by providing a pressure medium recovery capability which recycles the pressure medium from a surgical tourniquet cuff to the source of the higher pressure medium.

The flow control unit may also include a communications interface capable of receiving data from the remote unit. The data may include information associated with an operating profile for a surgical tourniquet. Minimally, the profile may include only a set pressure, allowing control over the inflation of any pressure cuffs attached to the flow control unit to be carried out by an operator. The profile may include a duration as well as a set pressure. Other information may be integrated into the profile to allow higher automation of control of the surgical tourniquet, such as the provision of threshold pressures which cannot be exceeded without direct operator intervention, durations which can not be exceeded without direct operator intervention, maximum pressures and durations, and functionality for control of multiple pressure cuff surgical tourniquets, such as those used in conjunction with localized anesthesia within the surgical region.

The remote unit may include an interface to allow an operator to control the profile of the surgical tourniquet. The interface may merely allow the operator to provide a set pressure, or may allow for the entry of complex profile parameters and the display of surgical tourniquet operational conditions, such as present pressure, display of any thresholds or maximum values, display of any durations set or time remaining under a set duration, or any other capability built into the flow control unit or remote unit. Although the flow control unit and the remote unit are contemplated as two separate devices, functions associated with these devices may be disseminated across more than two physical devices. An example of such a distribution would be the provision of a flow control processor in a computer located remotely from the surgical environment, while the operator interface and flow control valving are distributed between two devices in the operating environment. Accordingly, the remote unit also includes a communications interface to allow information in the remote unit to be transferred to the flow control unit, whether directly or indirectly, such as through a distributed flow control processor.

A pressure sensor may also be included in the flow control unit, allowing determinations of present pressure to be made for control purposes. Such a sensor does not need to be physically integrated with the flow control unit, but merely needs to be able to sense the pressure in a continuous volume of the pressure medium which includes the surgical tourniquet pressure cuff.

The flow control processor converts desired profile conditions into control signals for flow controls associated with the flow control unit. The flow control processor may use the output of the pressure sensor as a feedback to profile performance, as well as may utilize information from other sensors as a means to control surgical tourniquet performance.

The surgical tourniquet controller may also be embodied in a system including a flow control means for controlling the flow of a pressure medium into and out of a surgical tourniquet, and a remote unit means. The remote unit means for identifying parameters associated with controlling the operation of the flow control means. The remote unit means is located remotely from the flow control means, and is communicably connected to the flow control means via a communications path.

Although the present invention may be embodied in a system having a single operator interface located remotely from the flow control unit (referred to herein as the "remote unit"), redundant operator interfaces may be provided to reduce the potential impact of the failure of a remote unit on an on-going surgical procedure. A redundant interface may be provided on the flow control unit such that in the event of a failure of a remote unit or communications path, an operator may still successfully control the surgical tourniquet from the flow control unit.

In a more complex embodiment of the present invention, the surgical tourniquet flow controller may be embodied in a system having a surgical tourniquet pressurization manifold The manifold may have at least one pressure supply port and at least one pressure control valve, allowing the pressure in a surgical tourniquet connected to the manifold to be varied. A flow control processor may be provided for controlling the at least one pressure control valve in accordance with a pressure profile. The pressure profile may be defined at least in part by a parameter defining an operating condition of a surgical tourniquet The parameter may be a duration, desired pressure, or maximum allowable pressure value. The flow control processor may also include a communications interface for receiving information entered into a remote unit or other operating interface.

The present invention may also be embodied in a method for controlling at least one surgical tourniquet pressure cuff. Such a method includes the steps of providing a flow control unit adjacent to a surgical tourniquet pressure cuff, providing an operator interface remote from said flow control unit, providing a communications path between the flow control unit and the remote unit, receiving at the remote unit desired pressure cuff pressure parameters from an operator, communicating the desired cuff pressure parameters from the remote unit to the flow control unit via the first communications path, and pressurizing the at least one surgical tourniquet pressure cuff in accordance with the desired cuff pressure parameters.

Other features and advantages of the invention will be apparent from the following description of the preferred embodiment, and from the claims. Accordingly, reference should be made to the claims themselves

DETAILED DESCRIPTION OF THE INVENTION

Figure 1:
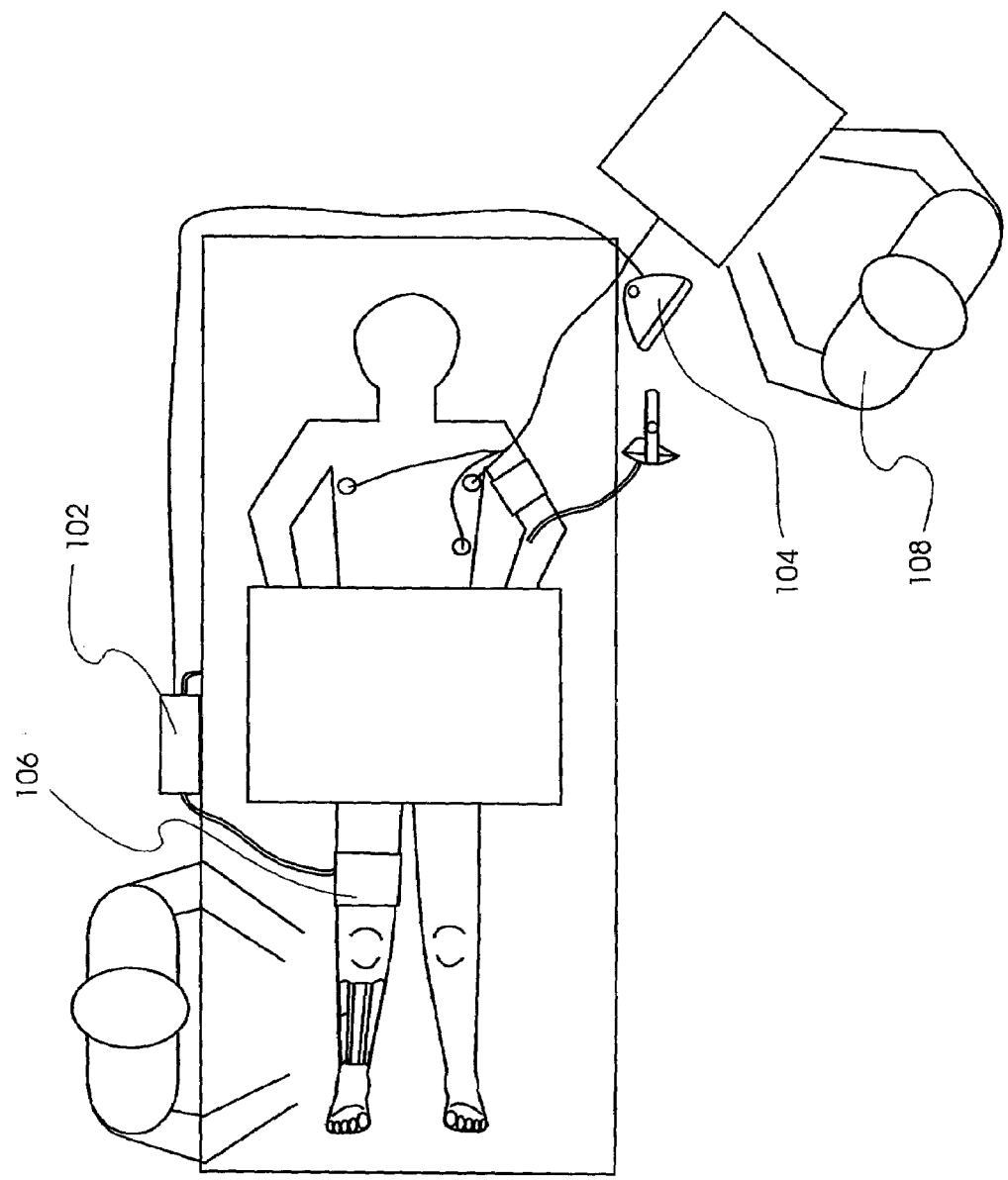
FIG. 1 illustrates the layout of an operating room configured for use in an operation involving placement of a surgical tourniquet on a lower extremity of a patient, wherein a surgical tourniquet controller according to the present invention is implemented for controlling the surgical tourniquet.

Referring particularly to FIG. 1, wherein like numerals represent like elements, there is shown a basic embodiment of a surgical tourniquet control system (hereafter "STCS") embodying the present invention. A flow control unit 102 and a remote unit 104 are provided. The flow control unit 102 (hereafter "FCU") may include flow control valves for controlling the pressure in a pressure cuff 106. Control circuitry for operating the valves may also be located in the FCU 102. The remote unit 104 provides an interface between an operator 102 of the surgical tourniquet control system and the flow control aspects of the system.

As shown in FIG. 1, the remote unit 104 may comprise a remote unit separate from the FCU 102 such that the remote unit 104 can be co-located with an anesthesiologist or other medical personnel 108 (hereafter referred to collectively as the "operator"). By providing the remote unit 104 at a location co-located with the operator 108 (such as when the anesthesiologist is the operator), the work load of the operator, when the operator is responsible for equipment or procedures beyond the surgical tourniquet, can be reduced by allowing the controls for the disparate equipment to be placed in a single location.

Figure 2:
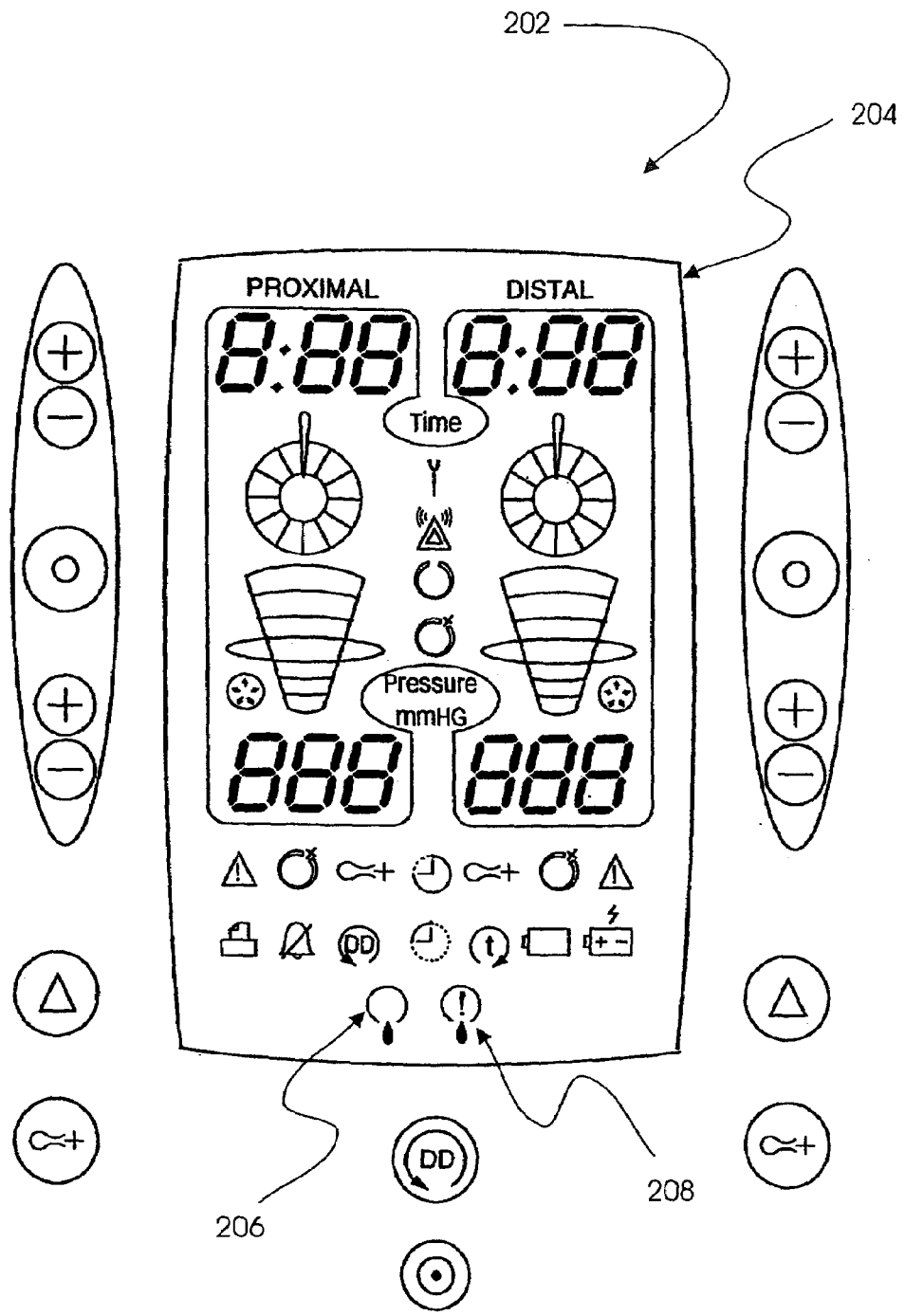
FIG. 2 illustrates a notional operator interface for a surgical tourniquet controller having a remote operator interface unit.

The remote unit 104 may include a graphical user interface 202 such as the one shown in FIG. 2. This interface illustrates some, but not all, of the indicators and controls that can be associated with monitoring and controlling the functionality of the FCU 102. The particulars of the graphical user interface selected may depend on the possible functions that the STCS is capable of performing. For example, where a timer is implemented into the STCS, the graphical user interface may include a display 204 showing the time remaining until the timer times out. Where the STCS incorporates flow feedback, as discussed in Applicant's co-pending U.S. patent application Ser. No. 09/955,763, herein incorporated in its entirety by reference thereto, the display may incorporate displays 206, 208 associated with flow conditions, such as whether flow is detected past a surgical tourniquet.

Figure 3:
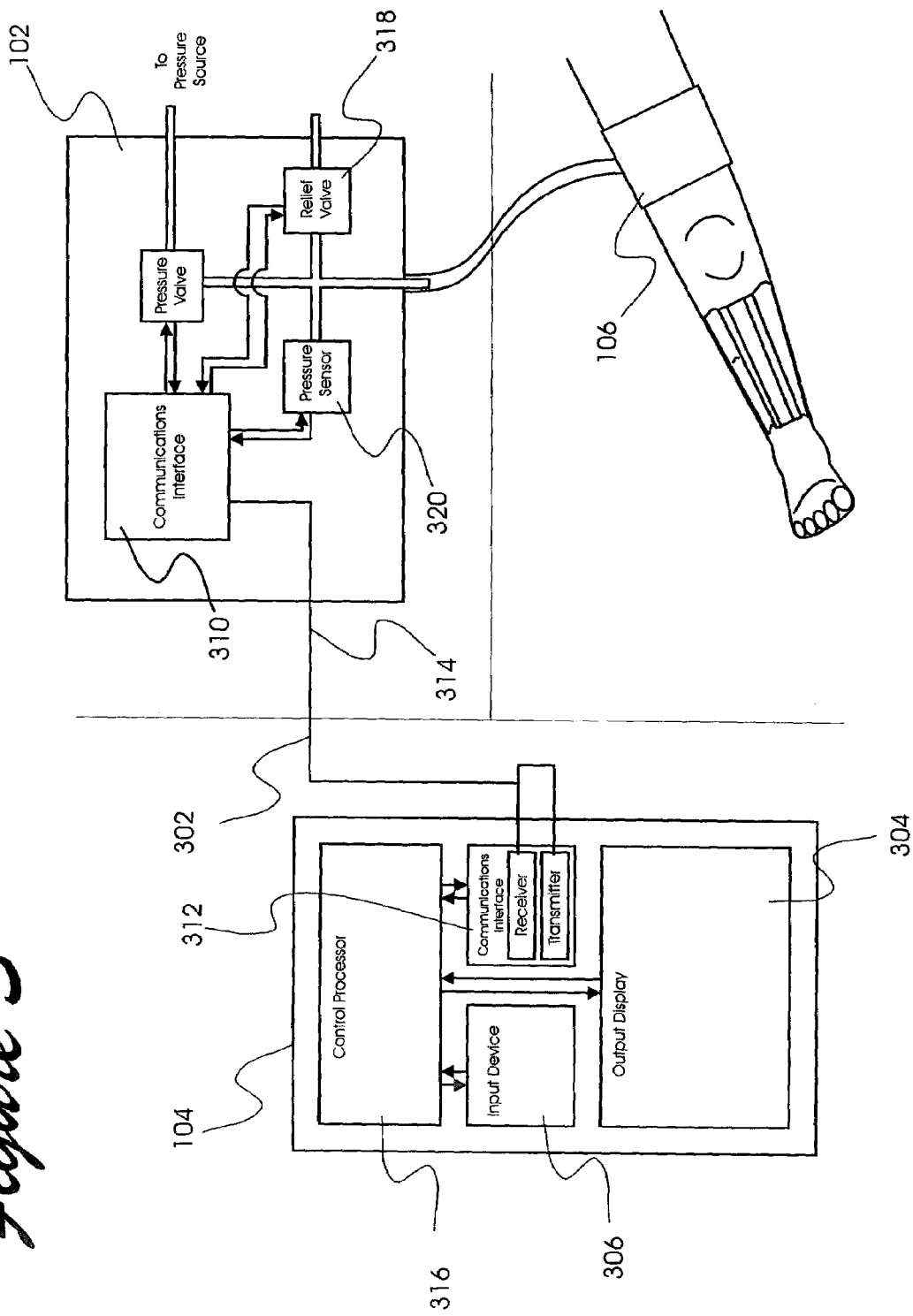
FIG. 3 illustrates the components of an embodiment of the present invention utilizing a hardwired connection as a communications path.

In a first embodiment, such as shown in FIG. 3, the FCU 102 and the remote unit 104 may be communicably connected through wires 302 which provide an electronic signal path between the units. The remote unit 104 itself may be configured to allow it to be mounted to an EKG display being used by an anesthesiologist, or may be configured as a standard rack-mountable component allowing incorporation of the remote unit 104 into a standard rack being used to house other components used in the surgical theater.

The remote unit 104 may incorporate an output display 204 to display parameters to an operator. The output display may be a small flat screen display. A flat screen display may incorporate an input device 306 such as touch sensing technology to allow interaction between an operator 108 and the output display 304 allowing the operator to select operational modes or values through interaction with the output display 304. Such a touch screen generally senses the touch at a location using screen coordinates, such as a touch at a certain row and column of the display. Software associated with the graphical user interface may be used to correlate the touch position with a control icon being displayed at the time the touch was detected. Accordingly, the touch screen can be used in coordination with the output display 304 to present a variety of indicators and controls in a single unit. The remote unit may also be provided with data logging capabilities, or data output capabilities, such as a printer or writeable media device.

The remote unit 104 may be configured such that it may be attached to standard equipment pole, such as discussed in Applicant's U.S. Pat. No. 6,051,016, herein incorporated in its entirety by reference thereto. The FCU may be provided with a pressure generation capability integral or may rely on an external pressure source.

The FCU 102 and remote unit 104 may preferably be configured with a minimum of surface features, such that the unit can be readily cleaned and sterilized. Such a minimum of surface features can be accomplished by limiting the presence of mechanical controls such as toggle or slide switches on either unit. The use of a touch screen assists in this endeavor.

Potential communication paths available for communicating data and instructions between an FCU and a remote unit include hardwiring, radio frequency transmission, and modulated light transmissions. Each data communication path has benefits and disadvantages when used in the surgical operating environment.

The simplest and likely most reliable method of providing a communications path between the FCU and the remote unit is to provide an electrically conductive wire 302 or wires between the FCU 102 and the remote unit 104. The electrically conductive path can be used to transmit modulated electrical signals from the FCU 102 to the remote unit 104, and vice versa. Technologies for transmitting modulated electrical signals between the units are known in the art, and generally incorporate some form of interface 310, 312 in each unit as shown in FIG. 3.

The use of a wired communications path may increase the amount of wiring present in the operating room, potentially causing trip hazards. Short circuits from frayed insulation, electronic noise emissions from inductance associated with current flow through the wires, and signal noise in transmitted signals (due to wiring lengths receiving stray emissions within the operating room) are other potential adverse consequences associated with the use of a hardwired communications path. Additionally, the cable used as the communications path must also be kept in a clean fashion, most likely in a sterile condition.

Where a wire path for communicably connecting the remote unit 104 to the FCU 102 is to be implemented, a power supply line for the controller may be bundled with the control wiring to limit the number of separate cables that must be present in the operating room. The generation of electronic noise from a hardwired communications path may be reduced by adequate shielding of the cable used as a communications path. The communications protocol used in the dedicated cable may be chosen for compatibility with other electronic equipment in the operating environment, such that the cable may function as a network bus to allow multiple pieces of equipment to monitor the communications over the dedicated cable.

Radio frequency (hereafter "RF") transmissions may be used to alleviate concerns over the presence of additional wiring in the operating room. RF transmissions can be accomplished in the operating room environment using low power transmitters to minimize the potential for effects between the emitted signals and other equipment in the operating theater. The benefits of RF transmissions as a communications path between the remote unit 104 and the FCU 102 are principally that the communications path does not require either a direct line of sight between the remote unit 104 and the FCU 102, nor hardwiring which may become a hazard in the operating theater.

RF transmitters, however, are direct sources of RF noise in the operating room, and can adversely effect other electronic equipment. Where combustible materials such as oxygen are in use, RF transmissions must be maintained at minimal levels, to avoid the creation of charge potentials in metal structures that could cause static discharge. These problems can be minimized by the use of low powered transmitters, sufficient to transmit over the short distances necessary between the remote unit 104 and the FCU 102.

Modulated light communications paths may also be used to transmit information between the Remote unit and the FCU, such as using modulated infrared light emitters and light sensitive elements in the Remote unit and FCU. The use of such technology is known.

The use of modulated light, such as infrared transmission, may be limited to line of sight, such that a visual path must be maintained between the transmitter and the receiver. Visual paths may also be susceptible to transient placement of objects between the remote unit and the controller, such as personnel in the operating theater, resulting in disruption of the communications path between the remote unit 104 and the FCU 102. Such infrared transmissions may also be limited in the data rate that can be achieved due to longer dwell times necessary for accurate reception of transmitted signals.

Alternately, modulated light can be transmitted using fiberoptic cables, creating a hardwired communications path using modulated light. Such a communications path has the advantage of not generating electronic emissions from the cabling, but retains the potential disadvantage of placing a cable in the operating environment.

In light of the above concerns, it is presently preferred that a hardwired communications path between the FCU 102 and the remote unit 104 be utilized. The hardwired path may be either a dedicated cable, or the use of a power cord where the communications signals between the FCU 102 and remote unit 104 can be imposed over the alternating current transmitted over the power cord.

As shown in FIG. 3, a hardwired communications path 314 may be provided between an FCU 102 communications interface 310 and a remote unit 104 communications interface 312. A control processor 316 may be provided to interpret operational parameters entered by an operator 108 (not shown) into a pressure profile at which a surgical tourniquet pressure cuff 106 is to be operated.

An input device 306 may be provided with the remote unit 104, such that an operator 108 (not shown) can indicate desired parameters. In a rudimentary form, the input device 306 merely needs to allow an operator 108 (not shown) to indicate a desired increase or decrease in a tourniquet pressure. The addition of an output display 304 to indicate operating conditions associated with the pressure cuff 106 allows the operator greater information upon which to base operating decisions. Incorporation of additional functionality into the FCU 102 or remote unit 104, such as but not limited to, a timer, allows presentations of additional functional constraints remaining to be displayed to an operator. Additional functions are described in the copending applications and patent incorporated herein.

The FCU 102 may also incorporate a relief valve 318 to allow pressure in a pressure cuff 106 to be reduced when desired, as well as a pressure sensor 320 to provide an indication of the occlusion potential of a pressure cuff 106 connected to the FCU 102. As occlusion of blood flow can be detected through dynamic monitoring of pressure in the pressure cuff 106, a pressure sensor 320 is not mandatory, but is rather a significantly useful capability.

As most operating rooms use clean or filtered power, ensured by the provision of dedicated power filters/sources for the operating room, the imposition of the communications signal over a power cord may be used to reduce the number of cables in an operating environment. Power cord transmission can be implemented using available protocols, such as "HOMEPLUG", promulgated by HomePlug Powerline Alliance, or through the use of a proprietary protocol. The use of power cord transmission may be limited where clean power is not provided in an operating room. In such a situation, noise in the transmitted AC current may limit the ability to clearly transmit signals from a controller to a Remote unit. Such noise may be present due to other electronic equipment utilizing the same power grid as a communications path, or from noise generated by electrical motors using the same power grid.

Figure 4:
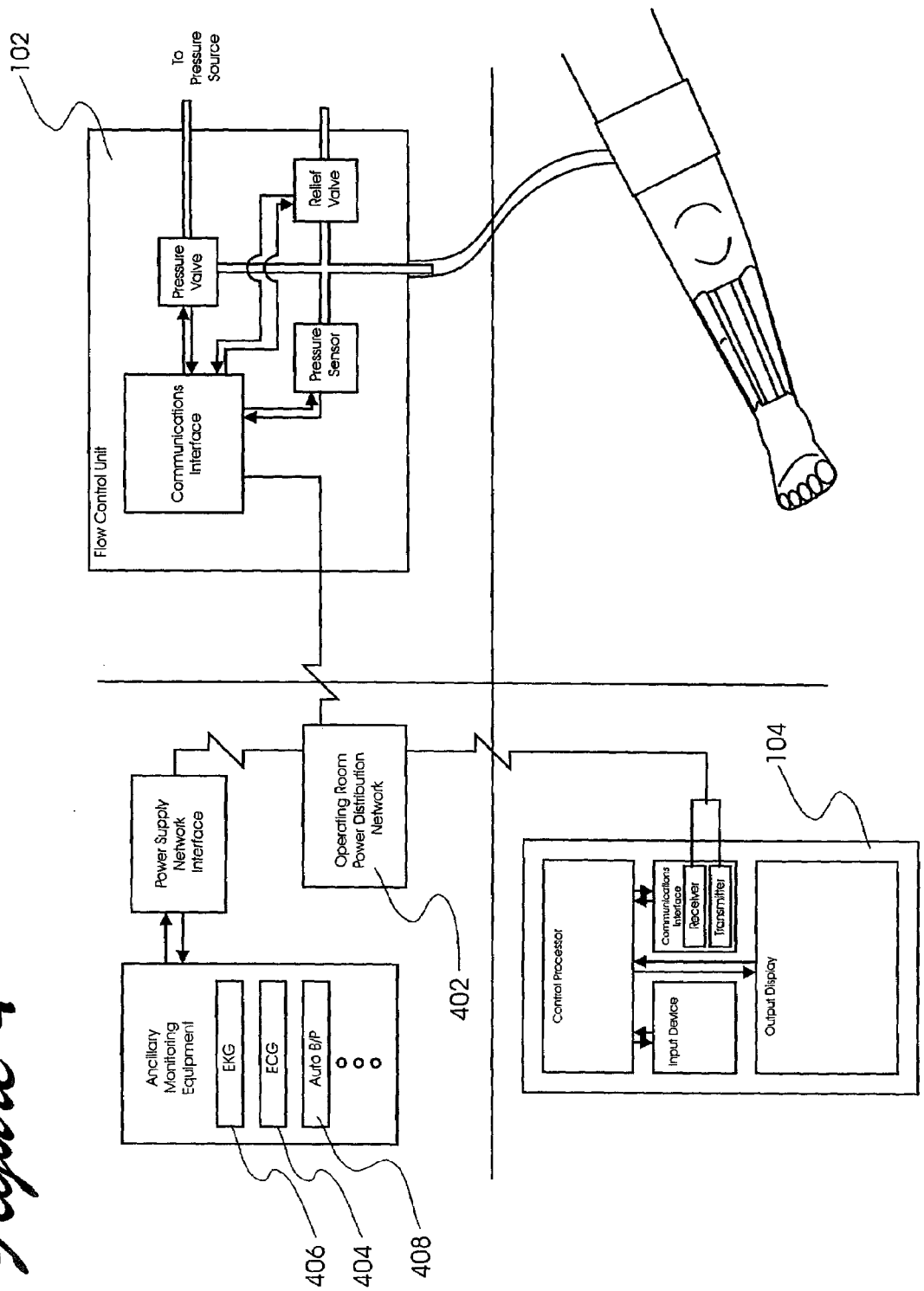
FIG. 4 illustrates an embodiment of the present invention utilizing a power distribution circuit as a communications path between a flow control unit and a remote unit.

A surgical tourniquet controller utilizing such a communications path is shown in FIG. 4. The FCU 102 and the remote unit 104 are both connected to the operating room power distribution network 402, such that communications between the FCU 102 and the remote unit 104 can be accomplished by multiplexing a signal coexistent with existing alternating or direct current. As shown in FIG. 4, additional devices may also be connected to the power network 402, allowing information from equipment such as, but not limited to, ECG 404, EKG 406, and automated blood pressure monitoring equipment 408 to be used to provide feedback to the surgical tourniquet controller system.

Figure 5:
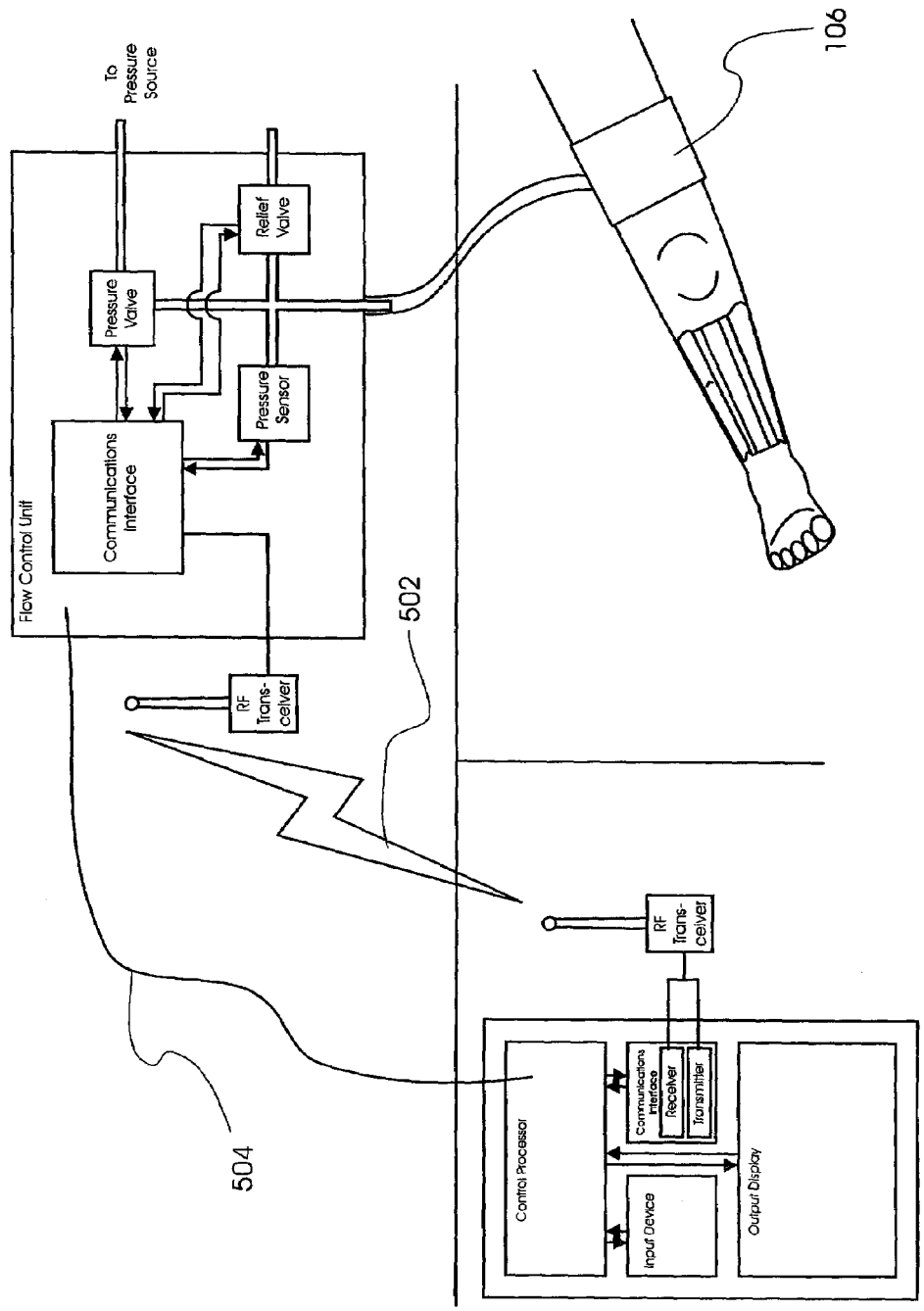
FIG. 5 illustrates an embodiment of the present invention utilizing both radio frequency transmissions between a flow control unit and a remote unit (and a hardwired communications path between the flow control unit and the remote unit.

As shown in FIG. 5, redundancies may be incorporated into the system to provide increased reliability. Multiple communications paths, such as an RF communications path 502 and a hardwired communications path 504 (such as using electrical signals or modulated light signals) may be provided such that loss of communications over one path does not prevent operation of a pressure cuff 106 from a remote unit 104.

Additionally, a redundant operator input device and output display (not shown) may be provided for the FCU 102, such that in the event of loss of communications over available communications paths, control of a pressure cuff 106 may be accomplished from the FCU 102. Such a redundant input and output capability may be a limited capability sufficient only to provide a minimal functionality, or be fully capable of controlling all functionality associated with the surgical tourniquet controller system.

Figure 6:
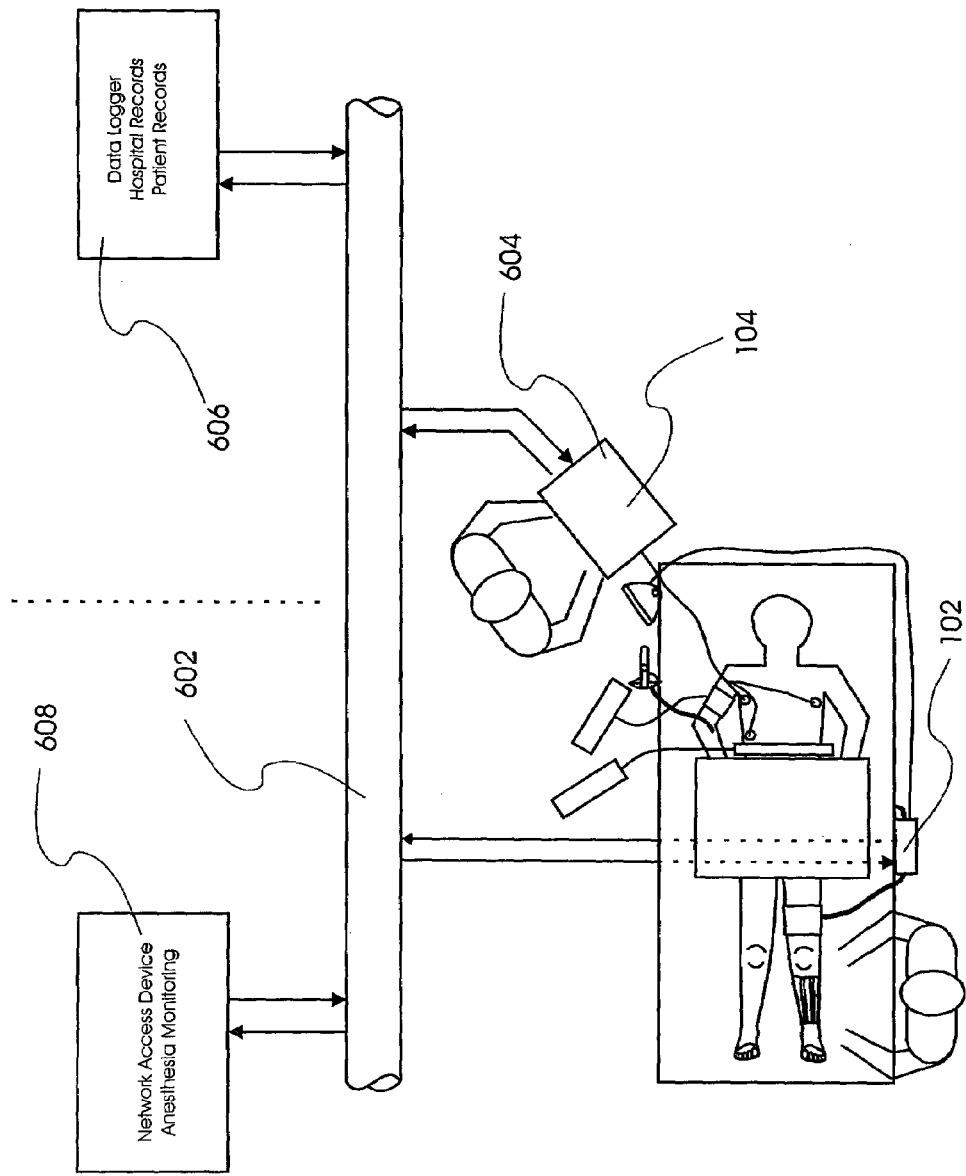
FIG. 6 illustrates an embodiment of the present invention wherein a computer network is utilized as the communications path to allow integration of the surgical tourniquet into the operating environment, shown in FIG. 6 by the provision of an integrated ECG monitor/remote unit, as well as the provision of a remote data logger and remote anesthesiology monitoring station.

The present invention may also be embodied in the apparatus shown in FIG. 6, wherein the FCU 102 is communicably connected to a computer network 602. A network access device connected 604 to the same computer network 602 is thus able to function as a remote unit 104 for the FCU 102, as well as to concurrently carry out other functions in the operating environment, such as functioning as an ECG or EKG monitor. Alternately, a network access device 606 may be located remotely from the operating environment, and function as a data logger, such that the network access device monitors the pressures associated with a surgical procedure, as well as the operator inputs, and the displays presented to the operator. Such a data logging function may be used to monitor the performance of the surgical tourniquet controller, as well as to allow correlation of operator performance with patient conditions exhibited during a procedure.

The use of a computer network as the communications path may further allow the flow controller to integrated with other equipment in the operating environment. Such a function is described in co-pending application Ser. No. 09/955, 763, which teaches the use of remote cardiac function monitoring, such as, but not limited to, automated blood pressure and respiration monitoring equipment as feedback for performance of a surgical tourniquet. Alternately, as described above, the integration into an operating environment network may allow improved dissemination of surgical tourniquet condition information to personnel dispersed throughout a surgical theater, as well as located remotely from the surgical theater, such as network device 608.

Figure 7:
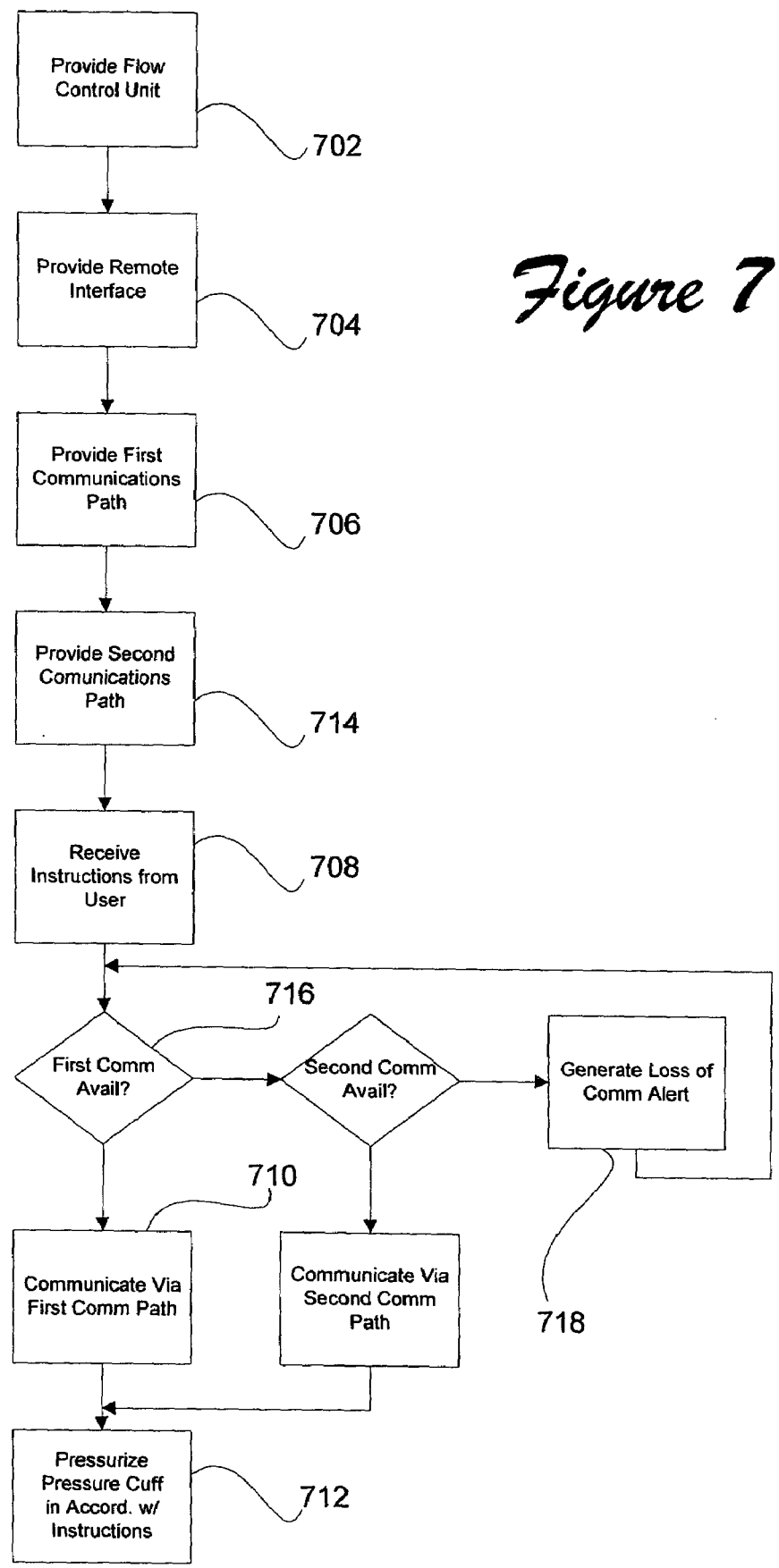
FIG. 7 illustrates the steps in a basic process for controlling a surgical tourniquet according to the present invention.

As shown in FIG. 7, the present invention may also be embodied in a method for providing a surgical tourniquet, comprising the steps of providing a flow control unit 702 adjacent to the location of a surgical tourniquet being used, providing an operator interface 704 remote from the flow control unit, and providing a communications path 706 between the flow control unit and the operator interface. An operator may then enter 708 desired operating parameters for the surgical tourniquet into the operator interface. The desired parameters are communicated 710 from the operator interface to the flow control unit, where a surgical tourniquet connected to the flow control unit can be pressurized 712 in accordance with the parameters. The parameters may be transformed into a pressure profile based on the parameters, or the parameters themselves may comprise the operating instructions to the flow control unit, such as the minimalist increase/decrease model discussed above.

The method may further comprise the step of providing a second 714 or redundant communications path between the flow control unit and the operator interface, such that should communications over the first communications path be degraded or lost, the second communications path may be used to ensure that an operator may continue to use the operator interface to control the flow control unit and surgical tourniquet pressurization.

When a second communications path is incorporated, the method may include checking to determine whether communications over a first communications path are available, such as by conducting a periodic request to communicate between the flow control unit and the operator interface to ensure that the communications path is valid. It may be preferable to limit such requests to periods when the flow control unit or operator interface are turned on, such that a signal can be generated 718 to alert an operator that communications between the flow control unit and the Remote unit have been lost, or that one communications path is not allowing communications.

The path checking function may also be implemented where only one communications channel has been provided, however the response associated with a detected loss of communications would be limited to generating a signal to warn an operator of the lost communications. Where redundant communications paths are implemented, communications between the flow control unit and the operator interface can be switched to a correctly functioning path in response to the detected loss of communications. Additionally, a signal can be generated under such circumstances, and a further signal can be used if every communications path suffers a loss of communications.

As is evident from the above description of the apparatus embodying the present invention, the method can be expanded to incorporate features associated with the disclosures of the copending applications, such as the use of occlusion sensors, more complex flow control systems, and feedback from ancillary equipment such as, but not limited to ECG and EKG sensors, without departing from the spirit or essential attributes of the invention.

Figure 8:
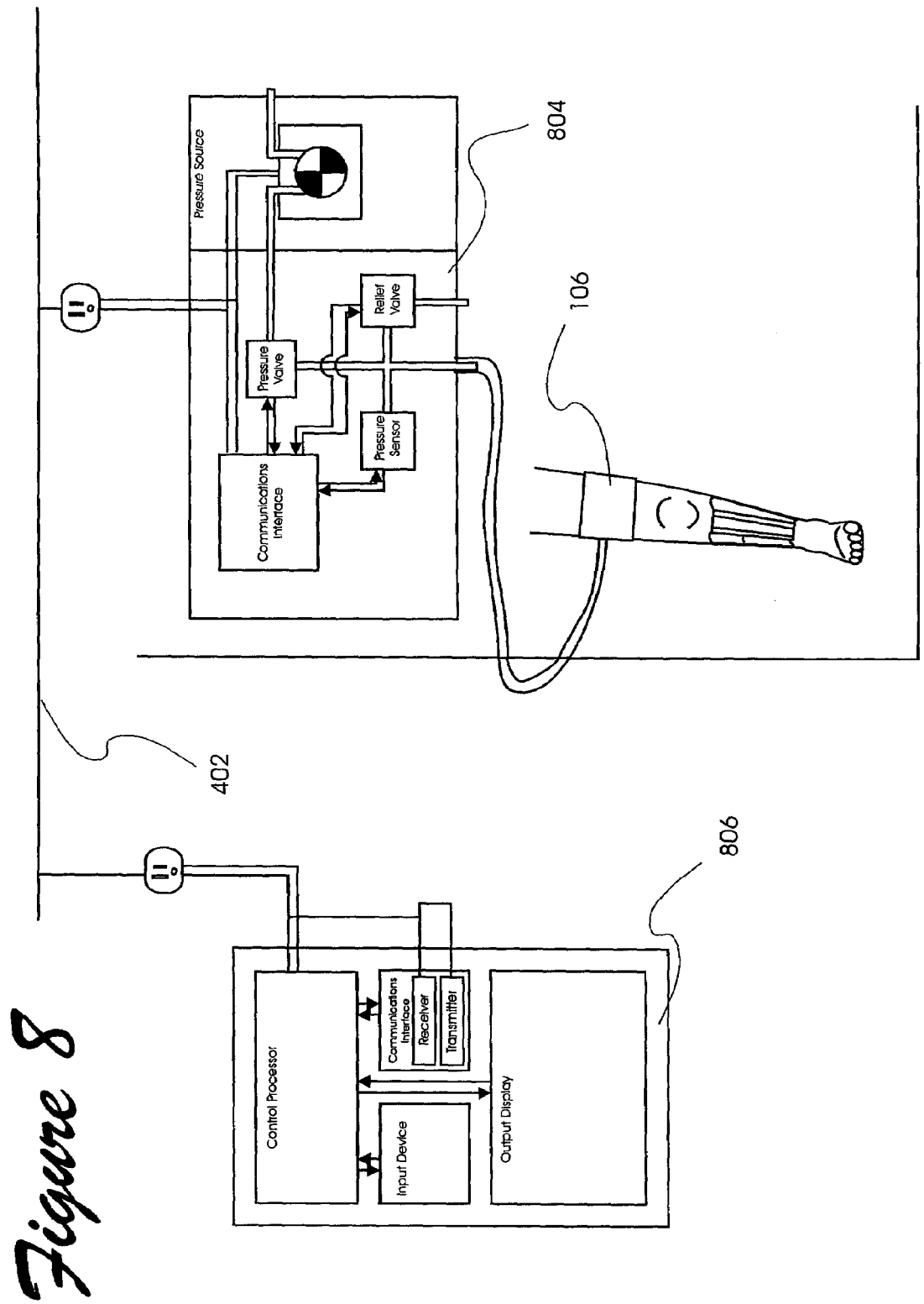
FIG. 8 illustrates an embodiment of the present invention wherein the flow control unit includes a pressure generation source to allow the use of a surgical tourniquet in conjunction with an operating table not originally configured for use with a surgical tourniquet.

As shown in FIG. 8, an additional benefit, such as embodied in the implementation shown in FIG. 8, is the ability to use the separation between the flow control unit and the Remote unit to simplify retrofitting a surgical tourniquet system to operating tables not originally configured for use with surgical tourniquets. Such tables may lack a pressure source for generating pressure for inflating a surgical tourniquet. Such tables will likely, however, have some provision for providing AC power. By incorporating a pressure generator 802, such as a small air compressor, into the flow control unit 804, the flow control unit 804 may combine all functionality required for supporting a surgical tourniquet. Further, by using a remote unit 806, accessibility requirements for the flow control unit are reduced, such that the flow control unit may be placed underneath the table, and thus out of the way with regard to the surgical field.

The present invention may be embodied in other specific forms without departing from the spirit or essential attributes of the invention. Accordingly, reference should be made to the appended claims, rather than the foregoing specification, as indicating the scope of the invention.

What is claimed is:

1. A surgical tourniquet controller, said controller comprising:
   a flow control unit, said flow control unit comprising at least one pressure control valve and a flow control unit communications interface; and
   a remote unit, said remote unit for controlling the at least one valve for controlling pressure, said remote unit comprising an input interface and a remote unit communications interface;
   a surgical tourniquet pressure sensor, said pressure sensor for sensing pressures in a surgical tourniquet cuff; and
   a flow control processor, said flow control processor controlling the at last one pressure control valve in accordance with a pressure profile, said pressure profile comprising at least one parameter defining an operating condition of a surgical tourniquet, said at least one parameter selected from a group of parameters consisting of duration, desired pressure, and maximum allowable pressure;
   wherein said input interface is able to accept entry of said at least one parameter, and wherein said remote unit communications interface is communicably connected to said flow control unit communications interface via at least one communications path, and further wherein said remote unit communications interface is capable of communicating said at least one parameter from the remote unit to the flow control processor via the at least one communications path.

2. A surgical tourniquet controller according to claim 1, wherein the communicable connection between the flow control communications interface and the Remote unit communications unit comprises a hardwired communications path.

3. A surgical tourniquet controller according to claim 2, wherein the hardwired communications path comprises a dedicated communications cable between said flow control communications interface and said remote unit communications interface.

4. A surgical tourniquet controller according to claim 2, wherein said hardwired communications path comprises a network bus for allowing multiple communications interfaces to communicate via the network bus.

5. A surgical tourniquet controller according to claim 2, wherein the Remote unit further comprises a power supply connected to a power supply network, the flow control unit further comprises a second power supply connected to the power supply network, and wherein said hardwired communications path comprises the power supply network.

6. A surgical tourniquet controller according to claim 2, wherein the communicable connection between the flow control unit communications interface and the remote unit communications interface comprises a radio frequency communications path.

7. A surgical tourniquet controller according to claim 1, wherein the Remote unit communications interface comprises a modulated light emitter, and the flow control unit communications interface comprises a modulated light receiver, and wherein said communicable connection between the flow control unit communications interface and the remote unit communications interface comprises a modulated light communications path.

8. A surgical tourniquet controller according to claim 7, wherein said communications path comprises a line of sight path between said remote unit communications interface and said flow control unit communications interface.

9. A surgical tourniquet controller according to claim 7, wherein said communications path comprises a fiber-optic link between said remote unit communications interface and said flow control unit communications interface.

10. A surgical tourniquet controller according to claim 1, wherein said Remote unit further comprises an output device, said output device capable of displaying a least one pressure condition, and wherein said flow control processor is communicably connected to said output device.

11. A surgical tourniquet controller according to claim 10, wherein said flow controller processor is integrated into said flow control unit, and further wherein said flow control unit communications interface is further capable of communicating pressures sensed by said pressure sensor to said output display.

12. A surgical tourniquet controller according to claim 11, wherein said output device is capable of displaying an operator entered parameter.

13. A surgical tourniquet controller according to claim 11, wherein said output device displays a graphical user interface, said graphical user interface for displaying a plurality of parameters and pressure conditions to an operator of said remote unit.

14. A surgical tourniquet controller according to claim 1, wherein said remote unit communications interface is communicably connected to said flow control unit communications interface via at least a first and a second communications path.

15. A surgical tourniquet controller according to claim 14, wherein said first communications path comprises a hardwired path, and where said second communications path comprises a radio frequency path.

16. A surgical tourniquet controller according to claim 14, wherein said first communications path comprises a hardwired path, and where said second communications path comprises a modulated light transmission path.

17. A surgical tourniquet controller according to claim 14, wherein the Remote unit further comprises a first power connection connected to a power supply network, the flow control unit further comprises a second power supply connection connected to the power supply network, and wherein said first communications path comprises a bus for allowing multiple communications interfaces to communicate via the bus, and where said second communications path comprises power supply network.

18. A surgical tourniquet controller according to claim 1, wherein said flow controller processor is integrated into said flow control unit, wherein said flow control unit, wherein said flow control unit communications interface is further capable of communicating pressures sensed by said pressure sensor to said output display, and wherein said flow control unit further comprises a redundant operator interface and a flow control output device, said flow control output device being capable of displaying at least one pressure condition.

19. A surgical tourniquet controller according to claim 18, wherein said flow controller processor further comprises a loss of communications path detector and a loss of communications signal.

20. A surgical tourniquet controller according to claim 18, wherein said remote unit communications further comprises a loss of communications path detector and a loss of communications signal.

21. A surgical tourniquet controller comprising:
a flow control means for controlling the flow of a pressure medium into and out of a surgical tourniquet; and
a remote unit means, said remote unit means for controlling the operation of the flow control means;
wherein said remote unit means is remote from said flow control means and said remote unit means is communicably connected to said flow control means via a communications path.

22. A surgical tourniquet controller for use in controlling the pressure in at least one surgical tourniquet pressure cuff according to claim 21, wherein said remote unit means comprises a display means and a data entry means, said display means for displaying parameters associated with pressurization of a pressure cuff, and wherein said data entry means is for receiving operator selections identifying desired operating parameters associated with pressurization of a pressure cuff.

23. A surgical tourniquet controller according to claim 21, wherein said display means comprises a plurality of light emitting diodes, at least a portion of said light emitting diodes arranged to display values identifying the pressure in a pressure cuff.

24. A surgical tourniquet controller according to claim 21, wherein said display means comprises a flat panel display.

25. A surgical tourniquet controller according to claim 21, wherein said display means comprises a cathode ray tube on which a graphical user interface may be displayed.

26. A surgical tourniquet controller to claim 21, wherein said data entry means comprises a plurality of switches, wherein actuation of said switches allows an operator of the remote unit to indicate desired parameters.

27. A surgical tourniquet controller according to claim 21, wherein said data entry means comprises a touch sensitive interface, said touch sensitive interface extending over at least a portion of said display means, and wherein said touch sensitive interface allows an operator of the remote unit to indicate desired parameters.

28. A surgical tourniquet controller according to claim 27, wherein said touch sensitive interface is actuable by a stylus.

29. A surgical tourniquet controller according to claim 27, wherein said touch sensitive interface is actuable by an operators finger.

30. A surgical tourniquet controller according to claim 21, wherein said remote unit comprises a computer, said computer having a display device, a pointing device, and a data entry device.

31. A surgical tourniquet controller according to claim 21, wherein said communications path comprises a modulated electrical signal communications means for communicating information between said remote unit means and said flow control means.

32. A surgical tourniquet controller according to claim 21, wherein said communications path comprises a modulated light signal communications means.

33. A surgical tourniquet controller according to claim 32, wherein said modulated light signal means comprises a fiber-optic connection.

34. A surgical tourniquet controller according to claim 21, wherein said communications path means comprises a radio frequency communications means.

35. A surgical tourniquet controller according to claim 21, wherein said first communications path comprises a first and a second communications path.

36. A surgical tourniquet controller according to claim 35, wherein said first communications path comprises a hardwired communications path.

37. A surgical tourniquet controller according to claim 35, wherein said first communications path comprises a computer network.

38. A surgical tourniquet controller according to claim 35, wherein said first communications path comprises a modulated light communications path.

39. A surgical tourniquet controller comprising:
   a flow control unit, said flow control unit comprising at least one pressure control valve, a flow controller, a first user interface, and a first communications interface, said first user interface comprising a user input device and a display device, said communications interface comprising at least a first and a second path interfaces;
   a remote unit, said remote unit comprising a second user interface and a second communications interface, said second user interface comprising a second user input device and a second display device, said second communications interface comprising at least a third and a fourth communications path interfaces;
   wherein said first path interface is communicably connected to said third path interface via a first communications path, and wherein said second path interface is communicably connected to said fourth path interface via a second communications path.

40. A surgical tourniquet flow controller, said surgical tourniquet flow controller comprising:
   a surgical tourniquet pressurization manifold, said manifold comprising at least one pressure supply port and at least one pressure control valve;
   a flow control processor, said flow control processor controlling the at last one pressure control valve in accordance with a pressure profile, said pressure profile comprising at least one parameter defining an operating condition of a surgical tourniquet, said at least one parameter selected from a group of parameters consisting of duration, desired pressure, and maximum allowable pressure; and
   a remote communications interface, said remote communications interface for receiving said at least one parameter from a remote entry device.

41. A surgical tourniquet controller according to claim 40, wherein said remote communications interface is communicably connected to a network access device, said network access device for accepting said at least one parameter from a user, and communicating said at least one parameter to said remote communications interface via a communications path, said communications path comprising a computer network.

42. A surgical tourniquet controller according to claim 41, wherein said network access device comprises a computer, said computer having surgical tourniquet controller software, said software comprising pressure profile entry and display functions.

43. A method for controlling at least one surgical tourniquet pressure cuff, comprising the steps of:
   providing a flow control unit adjacent to a surgical tourniquet pressure cuff;
   providing an operator interface remote from said flow control unit;
   providing a first communications path between said flow control unit and said remote unit;
   receiving at the remote unit desired pressure cuff pressure parameters from an operator;
   communicating said desired cuff pressure parameters from said remote unit to said flow control unit via the first communications path;
   pressurizing the at least one surgical tourniquet pressure cuff in accordance with said desired cuff pressure parameters;
   wherein said desired cuff parameters comprise inflated pressure and inflated duration.

44. A method for controlling at least one surgical tourniquet pressure cuff in accordance with claim 43, further comprising the step of providing a first communications path validity detector, said first validity detector determining whether said remote unit is in a communicable condition with said flow control unit when said flow control unit is energized, and signaling an alarm when said first validity detector determines that said remote unit is not in a communication with said flow control unit when said flow control unit is energized.

45. A method for controlling at least one surgical tourniquet pressure cuff in accordance with claim 44, further comprising the step of providing a second communications path, and further communicating said desired cuff pressure parameters from said remote unit to said flow control unit via the second communications path when said first validity detector determines that said remote unit is not in a communicable connection with said flow control unit when said flow control unit is energized.

* * * * *